United States Patent [19]

Meyer et al.

[11] Patent Number: 5,698,649
[45] Date of Patent: Dec. 16, 1997

[54] COPOLYMERS BASED ON VINYL ETHERS AND MONOETHYLENICALLY UNSATURATED DICARBOXYLIC ANHYDRIDES, THEIR PREPARATION AND THEIR USE

[75] Inventors: Harald Meyer, Deidesheim; Walter Denzinger, Speyer; Axel Sanner, Frankenthal; Hans Richter, Ludwigshafen; Hans-Juergen Raubenheimer, Ketsch; Franz Frosch, Bad Durkheim, all of Germany

[73] Assignee: BASF Aktiengesellschaft, Ludwigshafen, Germany

[21] Appl. No.: 645,047

[22] Filed: May 13, 1996

Related U.S. Application Data

[63] Continuation of Ser. No. 307,780, filed as PCT/EP93/01103 May 6, 1993 published as WO93/23445 Nov. 25, 1993, abandoned.

[30] Foreign Application Priority Data

May 16, 1992 [DE] Germany ............... 42 16 318.8

[51] Int. Cl.⁶ ............... C08F 222/06; C08F 222/10; C08F 216/14
[52] U.S. Cl. ............... 526/271; 526/321; 526/332
[58] Field of Search ............... 526/271, 321, 526/332

[56] References Cited

U.S. PATENT DOCUMENTS

| 3,436,378 | 4/1969 | Azorlosa. | |
|---|---|---|---|
| 3,530,010 | 9/1970 | Haynes et al. . | |
| 3,923,752 | 12/1975 | Güse et al. | 526/271 |
| 4,396,734 | 8/1983 | Williams et al. | 524/89 |
| 5,064,897 | 11/1991 | Tazi et al. . | |
| 5,187,308 | 2/1993 | Pelah et al. | 560/202 |

FOREIGN PATENT DOCUMENTS

| 70 09 85 | 8/1968 | Belgium . |
| 830 552 | 12/1969 | Canada . |
| 310 079 | 4/1989 | European Pat. Off. . |
| 428 956 | 5/1991 | European Pat. Off. . |
| 461 489 | 12/1991 | European Pat. Off. . |
| 1527411 | 3/1986 | France . |
| 1 930 009 | 12/1969 | Germany . |
| 58-25982 | 5/1983 | Japan . |
| 6810081 | 1/1969 | Netherlands . |
| 1209973 | 10/1970 | United Kingdom . |
| 1 233 168 | 5/1971 | United Kingdom . |

Primary Examiner—Joseph L. Schofer
Assistant Examiner—Wu C. Cheng
Attorney, Agent, or Firm—Keil & Weinkauf

[57] ABSTRACT

Copolymers which contain a) from 2 to 50 mol % of vinyl alkyl ethers having 3 to 30 carbon atoms in the molecule, b) from 10 to 88 mol % of monoethylenically unsaturated dicarboxylic anhydrides and c) from 10 to 88 mol % of dialkyl esters of monoethylenically unsaturated dicarboxylic acids as typical monomer units in polymerized form are prepared by copolymerizing the monomers a), b) and c) at from 40° to 180° C. in the presence of free radical initiators and are used as film-forming resins in hair sprays and, in the form of the alkali metal, ammonium or alkaline earth metal salts, as thickeners for aqueous systems, such as cosmetic and pharmaceutical formulations, textile print pastes, liquid detergents and cleaning agents.

13 Claims, No Drawings

COPOLYMERS BASED ON VINYL ETHERS AND MONOETHYLENICALLY UNSATURATED DICARBOXYLIC ANHYDRIDES, THEIR PREPARATION AND THEIR USE

This application is a continuation of application Ser. No. 08/307,780, filed as PCT/EP93/01103 May 6, 1993 published as WO93/23445 Nov. 25, 1993, now abandoned.

The present invention relates to copolymers of vinyl alkyl ethers, monoethylenically unsaturated dicarboxylic anhydrides and dialkyl esters of monoethylenically unsaturated dicarboxylic acids, processes for their preparation and their use as film-forming resins in hair sprays or in the form of water-soluble salts as thickeners for aqueous systems.

FR-A-1 527 411 discloses copolymers which consist of maleic anhydride, alkenes and vinyl alkyl ethers and are obtainable by precipitation polymerization of the monomers, for example in benzene, in the presence of free radical polymerization initiators. The anhydride group of the copolymers can be hydrolyzed and if necessary neutralized after the copolymerization.

BE-A-710 985 discloses terpolymers which are composed of vinyl alkyl ethers, maleic anhydride and a third monomer, for example acrylic acid, methacrylic acid, acrylamide, methacrylamide, vinyl chloride or styrene. The terpolymers are used in the paper industry. NE-A 68/10081 discloses that copolymers can be prepared from a) maleic anhydride, b) vinyl alkyl ethers, ethylene, propylene or vinyl acetate and c) 1-alkenes or long-chain vinyl alkyl ethers in inert solvents.

EP-A-0428956 discloses a process for the preparation of copolymers of monoalkyl maleates, vinyl alkyl ethers and maleic anhydride. In this process, an excess of vinyl alkyl ether is used as a solvent and precipitating agent. The specific viscosity or the chain length of the copolymer is controlled via the ratio of monoalkyl maleate to maleic anhydride.

U.S. Pat. No. 5,064,897 discloses the preparation of copolymers of monoalkyl maleates and vinyl alkyl ethers. A six-fold to ten-fold excess of vinyl alkyl ethers is used, and the monomeric monoalkyl maleate is prepared directly before the polymerization by reacting an alcohol with maleic anhydride in an equimolar ratio.

The reaction of polymers containing maleic anhydride units with alcohols in a polymer-analogous reaction is disclosed, for example, in the following publications: JP-A-1983/25 982, GB-A-1 233 468, DE-A-1 930 009, EP-A-03 10 079 and EP-A-04 61 489.

It is an object of the present invention to provide novel polymers and a process for their preparation.

We have found that the first-mentioned object is achieved by copolymers based on vinyl alkyl ethers and monoethylenically unsaturated dicarboxylic anhydrides, if the copolymers contain a) from 2 to 50 mol % of vinyl alkyl ethers having 3 to 30 carbon atoms in the molecule, b) from 10 to 88 mol % of monoethylenically unsaturated dicarboxylic anhydrides and c) from 10 to 88 mol % of dialkyl esters of monoethylenically unsaturated dicarboxylic acids as copolymerized units. We have found that the other object is achieved by a process for the preparation of the copolymers, if a) from 2 to 50 mol % of vinyl alkyl ethers having 3 to 30 carbon atoms in the molecule, b) from 10 to 88 mol % of monoethylenically unsaturated dicarboxylic anhydrides and c) from 10 to 88 mol % of dialkyl esters of monoethylenically unsaturated dicarboxylic acids are copolymerized at from 40° to 180° C. in the presence of initiators which form free radicals under the copolymerization conditions. The copolymers thus obtainable are used as film-forming resins in hair sprays or in the form of the alkali metal, ammonium or alkaline earth metal salts as thickeners for aqueous systems.

The copolymers contain, as monomers of component a) vinyl alkyl ethers having 3 to 30 carbon atoms in the molecule. Examples of suitable monomers of this type are vinyl methyl ether, vinyl ethyl ether, vinyl isopropyl ether, vinyl n-propyl ether, vinyl n-butyl ether, vinyl isobutyl ether, vinyl octyl ether, vinyl n-hexadecyl ether, vinyl n-octadecyl ether, vinyl n-eicosyl ether, vinyl n-hexacosyl ether and vinyl n-tricontyl ether. The copolymers may contain either a single vinyl ether or a mixture of a plurality of vinyl ethers as polymerized units. The copolymers preferably contain, as a monomer of group a), vinyl methyl ether, vinyl ethyl ether or vinyl octadecyl ether. The monomers of group a) are present in the copolymers in an amount of from 2 to 50, preferably from 25 to 50, mol %.

The copolymers contain, as monomers of group b), monoethylenically unsaturated dicarboxylic anhydrides which are preferably derived from compounds of 4 to 8 carbon atoms. Examples of suitable compounds of this type are maleic anhydride, itaconic anhydride, glutaconic anhydride, methylenemalonic anhydride, citraconic anhydride and mixtures of the stated anhydrides. The copolymers preferably contain maleic anhydride units. The amount of the monomers of group b) which are polymerized in the copolymers is from 10 to 88, preferably from 20 to 60, mol %.

The copolymers contain, c) dialkyl esters of monoethylenically unsaturated dicarboxylic acids as further characteristic monomers in polymerized form. The alkyl group of the esters may be derived from $C_1$–$C_{30}$-alcohols. The acid component of the esters is preferably formed from monoethylenically unsaturated dicarboxylic acids of 4 to 8 carbon atoms. Examples of the monomers c) are dialkyl esters of maleic acid, fumaric acid, itaconic acid, glutaconic acid, methylenemalonic acid and citraconic acid. The two alkyl radicals of the dialkyl ester may be either identical or different and are each, for example, methyl, ethyl, n-propyl, isopropyl, n-butyl, isobutyl, sec-butyl, n-amyl, n-hexyl, n-octyl or n-octadecyl. The monomers of group c) may be present in the copolymer either alone or as a mixture with one another in copolymerized form. The copolymers preferably contain diethyl or di-n-butyl esters of maleic acid as polymerized units. The monomers of group c) are present in the copolymers in an amount of from 10 to 88, preferably from 20 to 60, mol %.

The copolymers are prepared by copolymerizing the monomers of groups a), b) and c) at from 40° to 180° C. in the presence of initiators which form free radicals under the copolymerization conditions. The copolymerization can be carried out by all known polymerization methods, for example as a solution or precipitation polymerization. Suitable inert solvents or precipitating agents which do not react with the monomers a) to c) under the copolymerization conditions are ketones, such as acetone, methyl ethyl ketone or diethyl ketone, aromatic compounds, such as benzene, toluene or xylene, esters, such as ethyl acetate, isopropyl acetate, isobutyl acetate or n-butyl acetate, and straight-chain and branched aliphatic or cycloaliphatic hydrocarbons, such as pentane, hexane, heptane, octane, isooctane, cyclohexane, diethylcyclohexane and dimethylcyclohexane.

However, the copolymers are particularly preferably prepared by mass copolymerization, ie. the presence of inert solvents or diluents is dispensed with in this procedure. The monomers may be initially taken in the polymerization apparatus at the beginning of the copolymerization or, in a preferred procedure, may be added to the polymerization reactor a little at a time or continuously during the copolymerization. The polymerization temperature is preferably from 50° to 140° C. The polymerization is usually carried out at a temperature at which the reaction mixture is liquid and can therefore be readily stirred. The duration of the polymerization is from about 1 to about 15 hours, the polymerization generally being complete in the course of from 2 to 9 hours. The copolymerization can be carried out at atmospheric pressure, reduced pressure, eg. 100 mbar, or superatmospheric pressure, eg. up to 50 bar or more.

Suitable initiators which form free radicals under the copolymerization conditions are preferably all those compounds which have a half-life of less than 3 hours at the polymerization temperature chosen in each case. If the polymerization is started at a low temperature and completed at a higher temperature, it is advantageous to employ at least two initiators which decompose at different temperatures, ie. first to use an initiator which decomposes at a low temperature for initiating the polymerization and then complete the main polymerization using an initiator which decomposes at a higher temperature.

For example, the initiators stated for the purpose may be used for the temperature ranges stated below.

Temperature: from 40° to 60° C.

Acetylcyclohexanesulfonyl peroxide, diacetyl peroxydicarbonate, dicyclohexyl peroxydicarbonate, di-2-ethylhexyl peroxydicarbonate, tert-butyl perneodecanoate, tert-amyl perneodecanoate, 2,2'-azobis-(4-methoxy-2,4-dimethylvaleronitrile), 2,2'-azobis-(2-amidinopropane) dihydrochloride or 2,2'-azobis-[2-(2-imidazolin-2-yl)-propane] dihydrochloride;

Temperature: from 60° to 80° C.

tert-Butyl perpivalate, tert-amyl perpivalate, dioctanoyl peroxide, dilauryl peroxide or 2,2'-azobis-(2,4-dimethylvaleronitrile);

Temperature: from 80° to 100° C.

Dibenzoyl peroxide, tert-butyl per-2-ethylhexanoate, tert-butyl permaleate, 2,2'-azobisisobutyronitrile or dimethyl 2,2'-azobisisobutyrate;

Temperature: from 100° to 120° C.

Bis-(tert-butylperoxy)-cyclohexane, tert-butyl peroxyisopropyl carbonate, tert-butyl peracetate, hydrogen peroxide, tert-butyl perbenzoate or tert-butyl per-3,5,5-trimethylhexanoate;

Temperature: from 120° to 140° C.

2,2-Bis-(tert-butylperoxy)-butane, dicumyl peroxide, di-tert-amyl peroxide or di-tert-butyl peroxide;

Temperature: >140° C.

p-Menthane hydroperoxide, pinane hydroperoxide, cumene hydroperoxide or tert-butyl hydroperoxide.

Preferred initiators are those which are in liquid form at room temperature.

If, in addition to the stated initiators, salts or complexes of heavy metals, for example copper, cobalt, manganese, iron, vanadium, nickel or chromium salts, or organic compounds, for example benzoin, dimethylaniline or ascorbic acid, are used, the half-lives of the stated free radical initiators can be reduced. For example, tert-butyl hydroperoxide can be activated with the addition of 5 ppm of copper acetylacetonate so that polymerization can be carried out at as low as 100° C.

From 0.01 to 20, preferably from 0.05 to 10, % by weight, based on the total weight of the monomers used in the polymerization, of a polymerization initiator or a mixture of a plurality of polymerization initiators are used. If heavy metals are employed as catalyst components, the amounts used are from 0.1 to 100 ppm, preferably from 0.5 to 10 ppm. It is often advantageous to use a combination of peroxide, reducing agent and heavy metal as redox catalyst.

The molecular weight of the copolymer prepared according to the invention can, if desired, be modified, ie. reduced, by adding regulators to the polymerization mixture. Sulfur compounds, such as thioethers or disulfides, halogen compounds, such as carbon tetrachloride or 1,1,1-tribromopropane, ethers, such as tetrahydrofuran, and aldehydes, eg. acetaldehyde or butyraldehyde, may be used as molecular weight regulators.

The K value of the resulting copolymers, which is a measure of the molecular weight, is established by a suitable choice of regulators, initiators, polymerization temperature and monomer concentration, if the copolymerization is carried out in an inert solvent or diluent. The K values are usually from 10 to 110, preferably from 15 to 80, the measurements being carried out in 1% strength by weight solutions in water, ethanol or cyclohexanone, depending on the solubility of the copolymers.

Apparatuses suitable for polymerization are conventional stirred kettles having anchor, paddle or impeller stirrers or multistage impusle counter-current agitators. Apparatuses which permit direct isolation of the solid product after the polymerization, for example paddle dryers, are suitable.

The copolymers containing anhydride groups may be subjected to a large number of polymer-analogous reactions. Thus, the anhydride groups are converted into the corresponding mono- or diesters, for example by the action of alcohols on the copolymers containing anhydride groups. For this purpose, methanol, ethanol, n-propanol, isopropanol, n-butanol, isobutanol or amyl alcohol may be added, for example, to a melt of the copolymers. The corresponding mono- or diesters are then obtained from the anhydride groups in the copolymer. The addition of water to the melt of the copolymers results in hydrolysis of the anhydride groups to carboxyl groups. If desired, the carboxyl groups of the copolymers may be neutralized. For example, alkali metal and alkaline earth metal bases as well as amines and ammonia can be used for this purpose. Examples of suitable bases are sodium hydroxide solution, potassium hydroxide solution, calcium hydroxide, magnesium oxide, magnesium hydroxide, sodium carbonate, sodium bicarbonate, calcium carbonate, calcium bicarbonate or amines, such as triethylamine, ethanolamine, diethanolamine, triethanolamine or ammonia. Depending on the conditions in the neutralization of the copolymers containing anhydride groups, either only the anhydride groups of the copolymers are hydrolyzed and neutralized or, in the strongly alkaline pH range, hydrolysis of the ester groups of the components c) is also effected. As a result, the concentration of carboxylate groups in the copolymer increases.

Modification of the copolymers containing anhydride groups with long-chain amines, for example stearylamine or palmitylamine, with formation of semiamides or mixtures of semiamides and copolymers neutralized with long-chain amines, gives products which are of interest in particular as antiredeposition inhibitors in low-phosphate or phosphate-free detergents.

The copolymers containing anhydride groups can be used for many different applications. In cosmetic formulations, they are suitable in the form of alcoholic solutions especially as film-forming resins in hair sprays. As neutralized aqueous copolymer solutions, they can be used as oral and dental hygiene agents against tartar, plaque and gingivitis and as assistants in denture pastes. In the form of their alkali metal, ammonium or alkaline earth metal salts, the novel copolymers are suitable as thickeners for aqueous systems, such as cosmetic and pharmaceutical formulations, textile print pastes, liquid detergents and cleaning agents. They are also used as emulsifiers, dispersants, washing assistants, textile sizes, water treatment agents and assistants in oil production.

The K values stated in the Examples below were measured according to H. Fikentscher in 1% strength by weight solutions in cyclohexanone or water at a pH of 7 using the sodium salt at 25° C., cf. H. Fikentscher, Cellulose-Chemie 13 (1932), 58–64 and 71–74. In all Examples, the copolymerization was carried out in the absence of oxygen, in a nitrogen atmosphere.

EXAMPLE 1

172 g of diethyl maleate (feed 1), 98 g of maleic anhydride (feed 2, in a heatable dropping funnel), 200 g of vinyl isobutyl ether (feed 3) and 12 g of tert-butyl perneodecanoate (feed 4) are introduced into appropriate metering vessels.

111 ml of feed 1, 10 ml of feed 3 and 3 ml of feed 4 are initially taken in a 2 l stirred container equipped with a stirrer, a heater, a reflux condenser and the prepared metering apparatuses as well as a gas inlet and outlet and are heated to 60° C. At this temperature, the remainder of feed 1, the remainder of feed 3 and feed 2 are metered in over 3 hours and the remainder of feed 4 in the course of 4 hours. Stirring is then carried out for a further hour at 80° C. 18 g of water are added to the resulting colorless highly viscous melt at this temperature and stirring is carried out for 1 hour. The mixture is cooled to 75° C., after which 480 g of ethanol are metered in over 15 minutes and stirring is carried out for 1 hour at this temperature. Cooling to 25° C. gives a clear, viscous polymer solution having a solids content of 48.1% by weight. The copolymer has a K value of 26.8 (1% strength by weight in cyclohexanone).

EXAMPLE 2

172 g of diethyl maleate (feed 1), 98 g of maleic anhydride (feed 2, in a heatable dropping funnel), 200 g of vinyl isobutyl ether (feed 3) and 10 g of tert-amyl perpivalate (feed 4) were introduced into appropriate metering vessels.

In a 2 l stirred container equipped with a stirrer, a heater, a reflux condenser, and metering apparatuses filled with the starting materials and a gas inlet and outlet, 111 ml of feed 1, 10 ml of feed 3 and 3 ml of feed 4 are initially taken and are heated to 80° C. At this temperature, the remainder of feed 1, the remainder of feed 3 and feed 2 are metered in over 4 hours and the remainder of feed 4 in the course of 5 hours. Stirring is then carried out for a further hour at 85° C. 500 g of water are added to the resulting colorless, highly viscous melt at this temperature in the course of 1 hour. Cooling to 25° C. gives a clear, viscous polymer solution having a solids content of 46.3% by weight. The copolymer has a K value of 84.3 (1% strength by weight in water as the Na salt).

EXAMPLE 3

172 g of diethyl maleate (feed 1), 98 g of maleic anhydride (feed 2, in a heatable dropping funnel), 190 g of vinyl isobutyl ether and 30 g of vinyl octadecyl ether (both together feed 3) and 12 g of tert-butyl perneodecanoate (feed 4) are introduced into appropriate metering vessels.

111 ml of feed 1, 10 ml of feed 3 and 3 ml of feed 4 are initially taken in a 2 l stirred container equipped as in Example 1 and are heated to 70° C. At this temperature, the remainder of feed 1, the remainder of feed 3 and feed 2 are metered in over 3 hours and the remainder of feed 4 in the course of 4 hours. Stirring is then carried out for a further hour at 90° C. 18 g of water are added to the resulting pale yellow highly viscous melt at this temperature and stirring is carried out for 1 hour. The mixture is cooled to 75° C., after which 480 g of ethanol are metered in over 15 minutes and stirring is carried out for 1 hour at this temperature. Cooling to 25° C. gives a clear, viscous polymer solution having a solids content of 46.0% by weight. The copolymer has a K value of 27.6 (1% strength by weight in cyclohexanone).

EXAMPLE 4

172 g of diethyl maleate (feed 1), 98 g of maleic anhydride (feed 2, in a heatable dropping funnel), 195 g of vinyl isobutyl ether and 15 g of vinyl octadecyl ether (both together feed 3) and 11 g of tert-butyl per-3,5,5-trimethylhexanoate (feed 4) are introduced into appropriate metering vessels.

111 ml of feed 1, 10 ml of feed 3 and 2.5 ml of feed 4 are initially taken in a 2 l stirred container equipped as in Example 1 and are heated to 110° C. At this temperature, the remainder of feed 1, the remainder of feed 3 and feed 2 are metered in over 6 hours and the remainder of feed 4 in the course of 7 hours. Stirring is then carried out for a further hour at 125° C. The resulting yellowish, viscous melt is cooled to 75° C., after which 500 g of ethanol are added over 30 minutes and stirring is carried out for 1 hour. Cooling to 25° C. gives a yellowish, viscous polymer solution having a solids content of 48.3% by weight. The copolymer has a K value of 34.2 (1% strength by weight in cyclohexanone).

EXAMPLE 5

Example 4 is repeated with the exceptions that polymerization is carried out with 12 g of tert-butyl perneodecanoate instead of 11 g of tert-butyl per-3,5,5-trimethylhexanoate and at 60° C. instead of at 110° C. A clear, viscous polymer solution having a solids content of 47.2% by weight is obtained. The copolymer has a K value of 29.3 (1% strength by weight in cyclohexanone).

EXAMPLE 6

Example 4 is repeated with the exceptions that polymerization is carried out with 15 g of cumene hydroperoxide instead of 11 g of tert-butyl per-3,5,5-trimethylhexanoate and at 165° C. instead of at 110° C. A yellow, clear, viscous polymer solution having a solids content of 45.3% by weight is obtained. The copolymer has a K value of 28.7 (1% strength by weight in cyclohexanone).

EXAMPLE 7

Example 4 is repeated with the exceptions that polymerization is carried out with 15 g of tert-butyl per-2-ethylhexanoate instead of 11 g of tert-butyl per-3,5,5-trimethylhexanoate and at 90° C. instead of at 110° C. A yellowish, clear, viscous polymer solution having a solids content of 45.9% by weight is obtained. The copolymer has a K value of 36.9 (1% strength by weight in cyclohexanone).

EXAMPLE 8

160 g of diethyl maleate (feed 1), 98 g of maleic anhydride (feed 2, in a heatable dropping funnel), 190 g of vinyl isobutyl ether and 30 g of vinyl octadecyl ether (both together feed 3) and 12 g of 2,2'-azobis-(2,4-dimethylvaleronitrile) dissolved in 12 g of diethyl maleate (feed 4) are introduced into appropriate metering vessels.

In a 2 l stirred container equipped as in Example 1, 109 ml of feed 1, 10 ml of feed 3 and 8 ml of feed 4 are initially taken and are heated to 80° C. At this temperature, the remainder of feed 1, the remainder of feed 3 and feed 2 are metered in over 4 hours and the remainder of feed 4 in the course of 5 hours. A further 1.5 g of 2,2'-azobis-(2,4-dimethylvaleronitrile) are then added and stirring is carried out for 1 hour at 90° C. 18 g of water are added to the resulting clear, viscous melt at this temperature and stirring is carried out for 1 hour. The mixture is cooled to 75° C., after which 480 g of ethanol are metered in over 15 minutes and stirring is carried out for 1 hour at this temperature. Cooling to 25° C. gives a clear, viscous polymer solution having a solids content of 50.3% by weight. The copolymer has a K value of 35.2 (1% strength by weight in cyclohexanone).

EXAMPLE 9

86 g of diethyl maleate (feed 1), 49 g of maleic anhydride (feed 2, in a heatable dropping funnel), 297 g of vinyl octadecyl ether (feed 3, in a heatable dropping funnel) and 12 g of tert-butyl perneodecanoate (feed 4) are introduced into appropriate metering vessels.

In a 2 l stirred container equipped as in Example 1, 55 ml of feed 1, 30 ml of feed 3 and 3 ml of feed 4 are initially taken and are heated to 60° C. At this temperature, the remainder of feed 1, the remainder of feed 3 and feed 2 are metered in over 3 hours and the remainder of feed 4 in the course of 4 hours. Stirring is then carried out for a further hour at 65° C. 500 g of ethanol are added to the resulting clear viscous melt in the course of 30 minutes, and stirring is carried out for 1 hour at 80° C. Cooling to 25° C. gives a clear, viscous polymer solution having a solids content of 50.2% by weight. The copolymer has a K value of 16.7 (1% strength by weight in cyclohexanone).

EXAMPLE 10

172 g of diethyl maleate (feed 1), 98 g of maleic anhydride (feed 2, in a heatable dropping funnel), 192 g of vinyl isobutyl ether and 25 g of vinyl octadecyl ether (both together feed 3) and 12 g of tert-amyl perneodecanoate (feed 4) are introduced into appropriate metering vessels.

In a 2 l stirred container equipped as in Example 1, 111 ml of feed 1, 10 ml of feed 3 and 3 ml of feed 4 are initially taken and are heated to 60° C. At this temperature, the remainder of feed 1, the remainder of feed 3 and feed 2 are metered in over 3 hours and the remainder of feed 4 in the course of 4 hours. Stirring is then carried out for a further hour at 75° C. 500 g of isopropanol are added to the resulting colorless, highly viscous melt at this temperature in the course of 1 hour and, after the end of the isopropanol feed, stirring is carried out for a further 2 hours. Cooling to 25° C. gives a clear, viscous solution having a solids content of 47.1% by weight. The copolymer has a K value of 29.1 (1% strength by weight in cyclohexanone).

EXAMPLE 11

172 g of diethyl maleate (feed 1), 98 g of maleic anhydride (feed 2, in a heatable dropping funnel), 116 g of vinyl methyl ether and 45 g of vinyl octadecyl ether (both together feed 3) and 12 g of tert-butyl perpivalate (feed 4) are introduced into appropriate metering vessels.

In a 2 l stirred container equipped as in Example 1, 111 ml of feed 1, 10 ml of feed 3 and 3 ml of feed 4 are initially taken and are heated to 60° C. At this temperature, the remainder of feed 1, the remainder of feed 3 and feed 2 are metered in over 3 hours and the remainder of feed 4 in the course of 4 hours. Stirring is then carried out for a further hour at 70° C. First 18 g of water and then, in the course of 1 hour, 500 g of ethanol are added to the resulting colorless, highly viscous melt at this temperature and, after the end of the ethanol feed, stirring is carried out for a further 2 hours. Cooling to 25° C. gives a clear, viscous polymer solution having a solids content of 48.4% by weight. The copolymer has a K value of 21.2 (1% strength by weight in cyclohexanone).

EXAMPLE 12

172 g of diethyl maleate (feed 1), 98 g of maleic anhydride (feed 2, in a heatable dropping funnel), 110 g of vinyl methyl ether and 30 g of vinyl octadecyl ether (both together feed 3) and 12 g of tert-butyl perneodecanoate (feed 4) are introduced into appropriate metering vessels.

In a 2 l stirred container equipped as in Example 1, 111 ml of feed 1, 10 ml of feed 3 and 3 ml of feed 4 are initially taken and are heated to 60° C. At this temperature, the remainder of feed 1, the remainder of feed 3 and feed 2 are metered in over 3 hours and the remainder of feed 4 in the course of 6 hours. Stirring is then carried out for a further hour at 75° C. First 18 g of water and then, in the course of 1 hour, 500 g of n-butanol are added to the resulting colorless, highly viscous melt at this temperature and, after the end of the alcohol feed, stirring is carried out for a further 2 hours. Cooling to 25° C. gives a clear, viscous polymer solution having a solids content of 46.9% by weight. The copolymer has a K value of 22.0 (1% strength by weight in cyclohexanone).

EXAMPLE 13

Example 12 is repeated with the exception that, instead of 18 g of water and then 500 g of n-butanol, 600 g of 10% strength by weight sodium hydroxide solution are added to the melt. A clear, aqueous polymer solution having a solids content of 46.4% by weight and a pH of 8.9 is obtained. The copolymer has a K value of 80.3 (1% strength by weight in water).

EXAMPLE 14

Example 12 is repeated with the exception that, instead of 18 g of water and then 500 g of n-butanol, 74 g of calcium hydroxide are added to the melt. Comminution gives a white amorphous powder which, as a 10% strength by weight solution, has a pH of 6.5. The copolymer has a K value of 79.1 (1% strength by weight in water).

EXAMPLE 15

Example 12 is repeated with the exception that, instead of 18 g of water and then 500 g of n-butanol, 60 g of isobutylamine are added to the melt at 70° C. After the addition of 400 g of water, a clear, viscous polymer solution having a solids content of 47.7% by weight is obtained. The copolymer has a K value of 57.3 (1% strength by weight in water).

EXAMPLE 16

206.4 g of diethyl maleate (feed 1), 78.4 g of maleic anhydride (feed 2, in a heatable dropping funnel), 200 g of vinyl isobutyl ether (feed 3) and 12 g of tertbutyl 2-ethylhexanoate (feed 4) are introduced into appropriate metering vessels.

In a 2 l stirred container equipped as in Example 1, 111 ml of feed 1, 10 ml of feed 3 and 3 ml of feed 4 are initially taken and are heated to 90° C. At this temperature, the remainder of feed 1, the remainder of feed 3 and feed 2 are metered in over 4 hours and the remainder of feed 4 in the course of 5 hours. Stirring is then carried out for a further hour at 100° C. First, at this temperature, 14 g of water and, after cooling to 80° C., in the course of 1 hour, 500 g of ethanol are added to the resulting colorless, highly viscous melt and stirring is carried out for a further 2 hours. Cooling to 25° C. gives a clear, viscous polymer solution having a solids content of 51.3% by weight. The copolymer has a K value of 25.2 (1% strength by weight in cyclohexanone). It is suitable as a film-forming resin in hair sprays, especially in pump sprays.

EXAMPLE 17

Example 16 is repeated with the exceptions that, instead of 206.4 g of diethyl maleate and 78.4 g of maleic anhydride, 68.8 g of diethyl maleate and 156.8 g of maleic anhydride are used. The initially taken mixture contains 68.8 g of diethyl maleate instead of 111 ml. 29 g of water are used instead of 14 g. A clear, viscous polymer solution having a solids content of 49.2% by weight is obtained. The copolymer has a K value of 27.1 (1% strength by weight in cyclohexanone) and can be used as a film-forming resin in pump-action hair sprays.

EXAMPLE 18

Example 16 is repeated with the exception that 206.4 g of diethyl fumarate are used instead of 206.4 g of diethyl maleate. A clear, viscous polymer solution having a solids content of 48.4% by weight is obtained. The copolymer has a K value of 20.2 (1% strength by weight in cyclohexanone).

EXAMPLE 19

Example 16 is repeated with the exception that 223.2 g of diethyl citraconate and 86.6 g of itaconic anhydride are used instead of 206.4 g of diethyl maleate and 78.4 g of maleic anhydride. A clear, viscous polymer solution having a solids content of 46.9% by weight is obtained. The copolymer has a K value of 18.3 (1% strength by weight in cyclohexanone). It is used as a film former in hair sprays.

EXAMPLE 20

Example 16 is repeated with the exceptions that 242.2 g of di-n-butyl glutaconate and 112.1 g of citraconic anhydride are used instead of 206.4 g of diethyl maleate and 78.4 g of maleic anhydride. 18 g of water are used instead of 14 g. A clear, viscous polymer solution having a solids content of 46.2% by weight is obtained. The copolymer has a K value of 19.9 (1% strength by weight in cyclohexanone). It is used as a film former in pump-action hair sprays.

EXAMPLE 21

Example 16 is repeated with the exception that 172.8 g of of di-n-hexyl maleate are used instead of 206.4 g of diethyl maleate. A clear, viscous polymer solution having a solids content of 49.5% by weight is obtained. The copolymer has a K value of 24.8 (1% strength by weight in cyclohexanone). It is used as a film-forming resin in hair sprays.

EXAMPLE 22

Example 16 is repeated with the exception that 340.8 g of of di-n-hexyl maleate are used instead of 206.4 g of diethyl maleate. A viscous polymer solution having a solids content of 60.3% by weight is obtained. The copolymer has a K value of 22.8 (1% strength by weight in cyclohexanone). It can be used as a film-forming resin in pump-action hair sprays.

EXAMPLE 23

Example 16 is repeated with the exceptions that 364.8 g of of di-n-butyl maleate and 39.2 g of maleic anhydride are used instead of 206.4 g of diethyl maleate and 78.4 g of maleic anhydride. 7 g of water are used instead of 14 g. A clear, viscous polymer solution having a solids content of 58.3% by weight is obtained. The copolymer has a K value of 17.2 (1% strength by weight in cyclohexanone). It is used as a film-forming resin in pump-action hair sprays, in an amount of 2–20% by weight.

EXAMPLE 24

172 g of diethyl maleate (feed 1), 98 g of maleic anhydride (feed 2, in a heatable dropping funnel), 116 g of vinyl methyl ether (feed 3, in a cooled dropping funnel) and 12 g of tert-butyl per-2-ethylhexanoate (feed 4) are introduced into appropriate metering vessels.

In a 2 l pressure reactor equipped with a stirrer, heater, a reflux condenser, the metering apparatuses filled with the starting materials and a gas inlet and outlet, 111 ml of feed 1, 10 ml of feed 3 and 3 ml of feed 4 are initially taken and are heated to 90° C. At this temperature and at not more than 3.5 bar, the remainder of feed 1, the remainder of feed 3 and feed 2 are metered in over 3 hours and the remainder of feed 4 in the course of 4 hours. Stirring is then carried out for a further hour at 100° C. 500 g of water are added to the resulting colorless, highly viscous melt at this temperature in the course of one hour at atmospheric pressure and stirring is carried out for a further 2 hours. Cooling to 25° C. gives a clear, viscous polymer solution having a solids content of 44.4% by weight. The copolymer has a K value of 85.6 (1% strength by weight in water, as the sodium salt). It is used as a thickener for aqueous systems in the cosmetic and pharmaceutical sectors and in textile print pastes, liquid detergents and cleaning agents.

EXAMPLE 25

364.8 g of diethyl maleate (feed 1), 156.8 g of maleic anhydride (feed 2, in a heatable dropping funnel), 80 g of vinyl isobutyl ether (feed 3) and 24 g of tertbutyl per-2-ethylhexanoate (feed 4) are introduced into appropriate metering vessels.

In a 2 l stirred container equipped as in Example 1, 111 ml of feed 1, 8 ml of feed 3 and 5 ml of feed 4 are initially taken and are heated to 90° C. At this temperature, the remainder of feed 1, the remainder of feed 3 and feed 2 are metered in over 4 hours and the remainder of feed 4 in the course of 5 hours. Stirring is then carried out for a further hour at 95° C. First 29 g of water and, after cooling to 80° C., in the course of one hour, 600 g of ethanol are added to the resulting pale yellow, highly viscous melt at this temperature and stirring is carried out for a further 2 hours. Cooling to 25° C. gives a clear, viscous polymer solution having a solids content of 52.1% by weight. The copolymer has a K value of 15.8 (1% strength by weight in cyclohexanone). It is used as a film former in pump-action hair sprays, in amounts of 2–20% by weight.

EXAMPLE 26

About 90 g of ethanol are separated off by azeotropic distillation from the aqueous polymer solution obtained according to Example 13, after the addition of 20 g of sodium hydroxide. A clear, aqueous polymer solution having a solids content of 57.3% by weight and a pH of 11.6 is obtained. The copolymer has a K value of 83.4 (1% strength by weight in water). It is used as a thickener for aqueous systems in the pharmaceutical and cosmetic sectors. In compositions with bactericides, it can be used in dental cosmetics as a plaque and tartar preventer and against gingivitis. It can also be used in liquid detergents and cleaning agents.

We claim:

1. A copolymer based on vinyl ethers and monoethylenically unsaturated dicarboxylic anhydrides, which consists essentially of
    (a) from 2 to 50 mol % of vinyl alkyl ethers having 3 to 30 carbon atoms in the molecule,
    (b) from 10 to 88 mol % of monoethylenically unsaturated dicarboxylic anhydrides and
    (c) from 20 to 60 mol % of dialkyl esters of monoethylenically unsaturated dicarboxylic acids
as copolymerized units.

2. A process for the preparation of a copolymer as defined in claim 1, wherein
    (a) from 2 to 50 mol % of vinyl alkyl ethers having 3 to 30 carbon atoms in the molecule,
    (b) from 10 to 88 mol % of monoethylenically unsaturated dicarboxylic anhydrides and
    (c) from 20 to 60 mol % of dialkyl esters of monoethylenically unsaturated dicarboxylic acids
are copolymerized at from 40° to 180° C. in the presence of initiators which form free radicals under the copolymerization conditions.

3. A hairspray composition containing a copolymer as defined in claim 1 as a film-forming resin.

4. A thickener composition for aqueous systems containing a copolymer as defined in claim 1 in the form of the alkali metal, ammonium or alkaline earth metal salt.

5. The copolymer of claims 1 wherein (a) is vinyl isobutyl ether, (b) is maleic anhydride and (c) is diethyl maleate.

6. The copolymer of claims 1 wherein (a) is a mixture of vinyl isobutyl ether and vinyl octadecyl ether, (b) is maleic anhydride and (c) is diethyl maleate.

7. The copolymer of claims 1 wherein (a) is vinyl octadecyl ether, (b) is maleic anhydride and (c) is diethyl maleate.

8. The copolymer of claims 1 wherein (a) is vinyl isobutyl ether, (b) is maleic anhydride and (c) is diethyl fumarate.

9. The copolymer of claims 1 wherein (a) is vinyl isobutyl ether, (b) is itaconic anhydride and (c) is diethyl citraconate.

10. The copolymer of claims 1 wherein (a) is vinyl isobutyl ether, (b) is itaconic anhydride and (c) is diethyl citraconate.

11. The copolymer of claims 1 wherein (a) is vinyl isobutyl ether, (b) is maleic anhydride and (c) is di-n-hexyl maleate.

12. The copolymer of claims 1 wherein (a) is vinyl isobutyl ether, (b) is maleic anhydride and (c) is di-n-butyl maleate.

13. The copolymer of claims 1 wherein (a) is vinyl methyl ether, (b) is maleic anhydride and (c) is diethyl maleate.

* * * * *